United States Patent [19]

Becker et al.

[11] Patent Number: 4,973,736

[45] Date of Patent: Nov. 27, 1990

[54] DIETHERS OF M- OR P-HYDROXYPHENOL

[75] Inventors: Rainer Becker, Bad Durkheim; Werner Hoffmann, Neuhofen; Heinz-Guenter Oeser, Dirmstein; Wolfgang Rohr, Wachenheim; Juergen Varwig, Heidelberg, all of Fed. Rep. of Germany

[73] Assignee: BASF Aktiengesellschaft, Ludwigshafen, Fed. Rep. of Germany

[21] Appl. No.: 395,192

[22] Filed: Aug. 15, 1989

Related U.S. Application Data

[60] Continuation of Ser. No. 56,317, May 29, 1987, abandoned, which is a continuation of Ser. No. 740,431, Jun. 3, 1985, abandoned, which is a division of Ser. No. 444,846, Nov. 26, 1982, abandoned.

[30] Foreign Application Priority Data

Dec. 28, 1981 [DE] Fed. Rep. of Germany ....... 3151589

[51] Int. Cl.$^5$ .............................................. C07C 69/76
[52] U.S. Cl. ..................................... 560/61; 568/637; 568/649; 558/419; 558/421; 558/424
[58] Field of Search .................. 560/61; 568/637, 649; 558/419, 421, 424

[56] References Cited

U.S. PATENT DOCUMENTS 4,046,553  9/1977  Takahashi et al. .............. 544/131 X
4,248,618  2/1981  Serban et al. ................... 544/122 X

FOREIGN PATENT DOCUMENTS 18936  2/1981  Japan ..................................... 560/55

OTHER PUBLICATIONS

Jakobsen, et al., Chem. Abstracts, vol. 66, (1967), entry 80393f.
Derwent Abstract 48802 D/27 C02 of JP56-057769, May 20, 1981.
Czeswinska, et al., Chem. Abstracts, vol. 7, (1967) entry 73275m.
Ciba, *Chemical Abstracts*, vol. 57, No. 734a, (1962).
Clayton et al., *Chemical Abstracts*, vol. 77, No. 15624v (1972).

*Primary Examiner*—Bruce Gray
*Attorney, Agent, or Firm*—John H. Shurtleff

[57] ABSTRACT

Diethers of m- or p-hydroxyphenol, as well as the monoethers, are prepared by reacting m- or p-tert.-butoxyphenol of the formula II

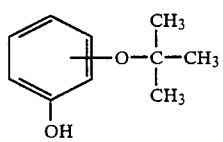

with a halogen compound in the presence of a hydroxide, carbonate and/or bicarbonate of an alkali metal or alkaline earth metal and an organic solvent which is inert under the reaction conditions, at from 20° C. to 150° C., and, if desired, reacting the resulting diether with a dilute aqueous inorganic acid at from 30° to 100° C. to give the monoether.

The end products which can be prepared by the process according to the invention are useful starting materials for the preparation of dyes, drugs and crop protection agents.

3 Claims, No Drawings

DIETHERS OF M- OR P-HYDROXYPHENOL

This application is a continuation of application Ser. No. 56,317 filed May 29, 1987, which in turn is a continuation of application Ser. No. 740,431 filed June 3, 1985, which in turn is a divisional of application Ser. No. 444,846, filed Nov. 26, 1982, all now abandoned.

The present invention relates to diethers of α- or p-hydroxyphenol and a process for the preparation of the diethers and monoethers of m- or p-hydroxyphenol by reacting m- or p-tert.-butoxyphenol of the formula II

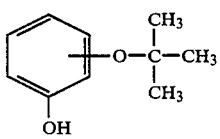

with a halogen compound in the presence of a hydroxide, carbonate and/or bicarbonate of an alkali metal or alkaline earth metal and an organic solvent which is inert under the reaction conditions, at from 20° C. to 150° C., and, if desired, reacting the resulting diether with a dilute aqueous inorganic acid at from 30°°–100° C. to give the monoether.

Etherification of hydroxyl group of hydroquinone or resorcinol with an olefinic, aromatic or heterocyclic radical is difficult to effect and produces relatively good yields only in special cases. However, a large excess of hydroquinone or resorcinol is as a rule necessary, which is uneconomical.

The synthesis proceeds substantially more simply and more uniformly if a protective group is used (European Patent Application No. 0,017,767). For example, hydroquinone monomethyl or monobenzyl ether is used as the starting material and is first etherified on the still free hydroxyl group with an olefinic, aromatic or heterocyclic radical, and the protective group is then split off again. The difficulties of this synthesis route arise, however, in the specific detachment of the protective group. As our own experiments have shown, the methyl radical can be successfully removed only under quite drastic conditions, for example with acetic acid/hydrobromic acid under reflux, with reaction times of several days. Cleavage of the second ether bond also occurs, so that such processes are uneconomical.

Japanese Preliminary Published Application No. 55 160-762 discloses that the benzyl protective group can be split off by catalytic hydrogenation with palladium-on-active-charcoal. Secondary reactions can also occur in this case, and in addition the method is complicated and thus uneconomical.

German Laid-Open Application DOS No. 2,546,251 discloses that a substituted halopyridine can be reacted with a p-($C_1$–$C_5$)-alkoxyphenol in the presence of an alkaline material to give the corresponding pyridyl alkoxyphenyl ether, and this can be converted into the corresponding pyridyl p-hydroxyphenyl ether by dealkylation. There are no embodiment examples or more detailed data in respect of dealkylation of the $C_1$–$C_5$ group. In particular, the tert.-butyl group is not described, nor arethe preparation and dealkylation of such tert.-butoxy compounds described in more detail or demonstrated with an example. Only reaction (a) preferably at 150°–200° C. using pyridine hydrochloride as the dealkylating agent, or (b) at a temperature close to the boiling point of a lower fatty acid used, as the solvent with a hydrogen halide acid as the dealkylating agent, is mentioned as a general form of dealkylation of $C_1$–$C_5$-alkoxy groups. Acetic acid and acetic anhydride are mentioned as the fatty acid, and hydrobromic acid and hydroiodic acid are mentioned as the hydrogen halide acid.

We have found that diethers of m- or p-hydroxyphenol, of the formula

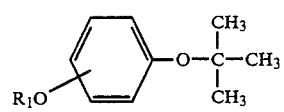

or monoethers of m- or p-hydroxyphenol, of the formula

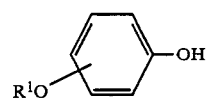

where the two hydroxyl groups are in the m- or p-position relative to one another and $R^1$ is an aliphatic radical or

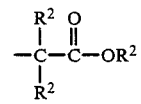

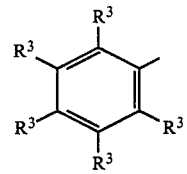

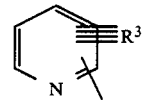

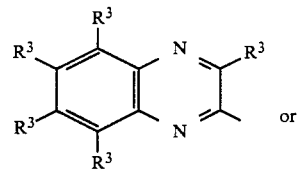

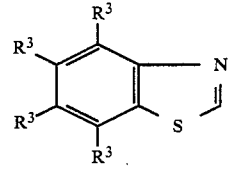

the individual radicals $R^2$ and $R^3$ can be identical or different and each is hydrogen or an aliphatic, araliphatic or aromatic radical, and $R^3$ can also in each case be halogen, nitro, cyano or alkoxy, are obtained in an advantageous manner by reacting a monoether of a dihydroxy compound with a halogen compound to form a diether and, if desired, splitting off the original monoether group, by a process wherein (a) m- or p-tert.-butoxyphenol of the formula

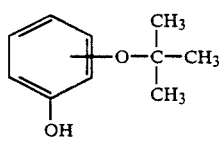

is reacted with a halogen compound of the formula

     III where $R^1$ has the above meanings and X is halogen, in the presence of a hydroxide, carbonate and/or bicarbonate of an alkali metal or alkaline earth metal and an organic solvent which is inert under the reaction conditions, at from 20° to 150° C., to give the end product Ia, and, if desired, (b) the resulting end product Ia is reacted with water, a water-miscible alkanol and an inorganic acid at from 30° to 100° C. to give the end product Ib.

The novel diethers of m- or p-hydroxyphenol, of the formula

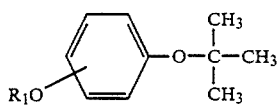     Ia where the two hydroxyl groups are in the m- or p-position relative to one another and $R^1$ is an aliphatic radical or

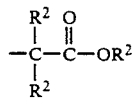

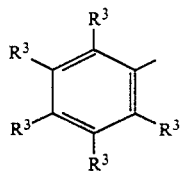

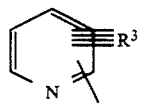

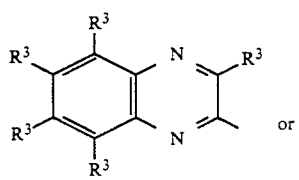     or

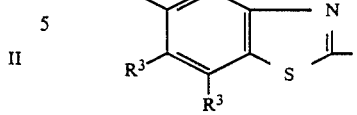     II and the individual radicals $R^2$ and $R^3$ can be identical or different and each is hydrogen or an aliphatic, araliphatic or aromatic radical, and $R^3$ can also in each case be halogen, nitro, cyano or alkoxy, have also been found.

If 2-chloro-5-nitropyridine, p-(tert.-butoxy)phenol and sodium hydroxide solution are used, the reaction can be represented by the following equation:

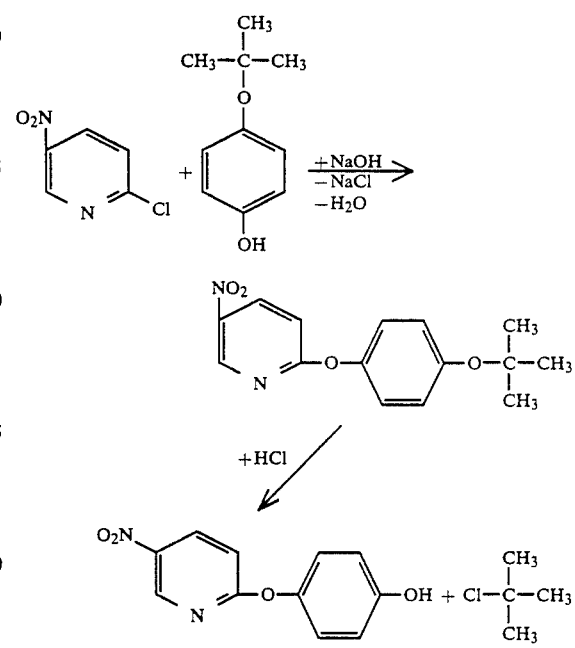

Compared to the prior art, the process according to the invention gives diethers or monoethers of p- or m-hydroxyphenol in a good yield and purity by a simple and economical route. At the same time, the novel diethers having a tert.-butoxy group as the ether component are characterized by embodiment examples. It had not hitherto been disclosed that this same tert.-butyl group is surprisingly split off from the novel diethers Ia more rapidly end/or at a lower temperature than other alkyl groups, such as the methyl group. Thus, compared to German Laid-Open Application DOS No. 2,546,251, the overall process (stages a) and b)) is simpler and more economical and produces a higher space/time yield. It is surprising that the conditions according to the invention in stage (a), and even more in stage (b), give good results not only with pyridyl ethers but advantageously also with other ether components which differ greatly from the pyridyl group. It is also unexpected that the very conditions according to the invention in stage (b), for example the use of alkanol and water, permit advantageous dealkylation of the novel end products Ia. It is also surprising that, compared to German Laid-Open Application DOS No. 2,546,251, the dealkylation does not have to be carried out at a temperature close to the boiling point of the solvent, and the advantageous results according to the invention can be achieved even without the addition of a lower fatty acid, e.g. acetic acid. At the same time, the milder reaction conditions enable even sensitive end products, e.g. fluoroalkoxy compounds, to be prepared.

The starting substances II and III can be reacted in stoichiometric amounts or with an excess of either component, based on the other, advantageously in a molar ratio of III to II of from 1 to 10:1, preferably from 1 to 2:1. Preferred starting substances II and III, and accordingly preferred end products Ia and Ib, are those in which the two hydroxyl groups are in the m- or p-position relative to one another, $R^1$ is alkyl of 1 to 6 carbon atoms, haloalkyl, preferably of 1 to 6 carbon atoms and substituted by 1 or 2 chlorine atoms and/or fluorine atoms, or

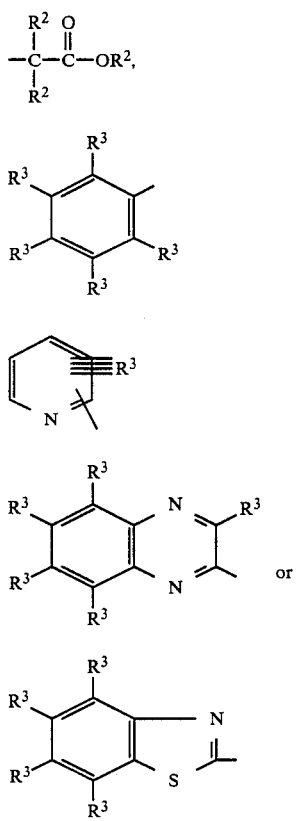

the individual radicals $R^2$ and $R^3$ can be identical or different and each is hydrogen, alkyl or 1 to 6 carbon atoms, which is unsubstituted or substituted by 1 or 2 chlorine and/or fluorine atoms, or aralkyl or alkylaryl of 7 12 carbon atoms or aryl of 6 to 10 carbon atoms, and $R^3$ can also in each case be chlorine, fluorine, nitro, trifluoromethyl, trichloromethyl, cyano or alkoxy of 1 to 6 carbon atoms, and X is chlorine or fluorine. The above radicals can also be substituted by groups which are inert under the reaction conditions, e.g. alkyl or alkoxy, each 1 to 4 carbon atoms.

Examples of suitable starting substances III are methyl, ethyl, propyl, isopropyl, butyl, sec.-butyl, isobutyl and tert.-butyl chloride or fluoride, α-chloroacetic acid, α-fluoroacetic acid, corresponding α-chloroacetic or α-fluoroacetic acids which are monosubstituted or disubstituted in the α-position by the methyl, ethyl, propyl, isopropyl, butyl, isobutyl, sec.-butyl, tert.-butyl, phenyl, xylyl or benzyl group, and the corresponding methyl, ethyl, propyl, isopropyl, butyl, isobutyl, sec.-butyl, tert.-butyl, benzyl, xylyl and phenyl esters, and phenyl chloride or fluoride, pyridine 2- or 4-chloride or -fluoride, quinoxaline chloride or fluoride, or benzothiazole 2-chloride or -fluoride, each of which is unsubstituted or substituted by alkyl, chloroalkyl or fluoroalkyl of 1 to 4 carbon atoms and, where relevant, 1 or 2 halogen atoms, in particular chlorine or fluorine atoms, or by aralkyl of 7 to 12 carbon atoms, aryl of 6 to 10 carbon atoms, chlorine, fluorine, nitro, cyano or alkoxy of 1 to 4 carbon atoms. In general, in addition to the halogen atoms, 1 to 2 of the above substituents are present on the aromatic or heterocyclic ring, or the rings are unsubstituted.

Preferred starting substances III are chlorodifluoromethane, 4-trifluoro- and 4-trichloro-methylphenyl chloride, 4-nitrophenyl 1,2-dichloride, 2-chloro-5-iodo-phenyl chloride, 4-nitrophenyl chloride, 2-chloro-4-nitropyridine, 2,3,5-trichlorobenzene, 2,6-dichloroquinoxaline, 2-chlorobenzothiazole, methyl, ethyl, propyl, n-butyl and isobutyl α-bromopropionate or α-chloropropionate, 2-nitro-4-trifluoromethylchlorobenzene, 2-bromo-5-iodopyridine, 2-chloro-5-nitropyridine, 2-bromo-3,5-dichloropyridine and 2,3,5-trichloropyridine.

p-(tert.-Butoxy)-phenol can be prepared in a conventional manner (J. Chromatogr. 10 (1963), 42 to 67; and C.A. 60, 6773 b). The m-compound is synthesized in a similar manner.

The reaction is carried out in stage (a) at from 20° C. to 150° C., preferably from 20° C. to 100° C., and in stage b) at from 30 to 100° C., preferably from 40 to 100° C. and in particular from 45° to 80° C., under atmosphereic or superatmospheric pressure, batchwise or continuously. Sodium, potassium and calcium are the preferred cations in the hydroxide, carbonate and bicarbonate catalysts. A ratio of from 1 to 10, preferably from 1 to 1.5, equivalents of alkali metal or alkaline earth metal compound per mole of starting substance III is advantageous.

Organic solvents which are inert under the reaction conditions are used in stage (a), for example alkanols and cycloalkanols, e.g. ethanol, methanol, n-butanol, isobutanol, tert.-butanol, glycol, glycerol, sec.-butanol, n-propanol, isopropanol, amyl alcohol, cyclohexanol, 2-methyl-4-pentanol, ethylene glycol monoethyl ether, 2-ethylhexanol, methylglycol, n-hexanol, isohexyl alcohol, isoheptyl alcohol, n-heptanol, ethylbutanol, nonyl alcohol, dodecyl alcohol, methylcyclo hexanol and diacetone alcohol, and especially those of 1 to 6 carbon atoms, carbon disulfide, dioxane, tetrahydrofuran, sulfoxides, e.g. dimethylsulfoxide and diethylsulfoxide, dimethylsulfone, diethylsulfone, methylethylsulfone and tetramethylenesulfone, and appropriate mixtures. The amount of solvent is advantageously from 400 to 10,000 per cent by weight, preferably from 400 to 2,000 per cent by weight, based on the starting substance II.

The treatment of the end product Ia in stage b) is carried out in the presence of an acid, advantageously with from 0.001 to 1, in particular from 0.01 to 0.1, equivalent of acid per mole of end product Ia. Inorganic acids are used. Instead of a monobasic acid, it is also possible to use an equivalent amount of a polybasic acid. Examples of suitable acids are hydrochloric acid, hydrobromic acid, hydroiodic acid, perchloric acid, sulfuric acid, phosphoric acid, nitrous acid, nitric acid and carbonic acid. Dilute, aqueous acids are advantageously from 1 to 20 per cent strength by weight, for example 1-20 per cent strength by weight hydrochloric acid, 1-20 per cent strength by weight sulfuric acid or 1-20 per cent strength by weight phosphoric acid. Hydrochloric acid, phosphoric acid and, in particular, sulfuric acid are preferred.

The alkanol used is generally completely water-miscible, and is advantageously methanol or ethanol. The quantities used are advantageously from 0.1 to 1,000, in particular from 0.1 to 100, grams of water, including the water content of the dilute acid, and from 1 to 10,000, in particular from 1 to 100, grams of alcohol per gram of end product Ia. A combination of from 0.1 to 1,000 grams of water and from 0.1 to 1,000 grams of alkanol per gram of acid, especially sulfuric acid, is particularly preferred.

The reaction can be carried out by keeping the starting substance II and III, the basic catalyst and the solvent at the reaction temperature for from 0.5 to 5 hours. The end product Ia is then isolated in a conventional manner, for example by addition of water and acid until the pH is 3, filtration with suction, and washing of the solid material which has separated out. If desired, the end product Ia is kept at the reaction temperature of stage b) in a mixture of alkanol, water and inorganic acid for from 0.5 to 10 hours. The resulting end product Ib is isolated from the mixture in a conventional manner, for example by addition of water, neutralization with, for example, sodium hydroxide solution, filtration with suction and washing.

The end products Ia and Ib which can be prepared by the process of the invention are useful starting materials for the preparation of dyes, drugs and crop protection agents. Thus, for example, the crop protection agents disclosed in German Laid-Open Applications DOS 2,433,067 (U.S. Pat. No. 4,332,960), DOS 2,223,894 (U.S. Pat. No. 3,954,442), DOS 3,004,770 (U.S. Pat. No. 4,629,493) and DOS 2,546,251 (U.S. Pat. No. 4,083,714, U.S. Pat. No. 4,092,151, and U.S. Pat. No. 4,115,102) and in European Patent Application 0,002,246 (U.S. Pat. Nos. 4,200,587 and 4,380,661). For example, the following compounds can be prepared from the intermediates Ia and Ib:

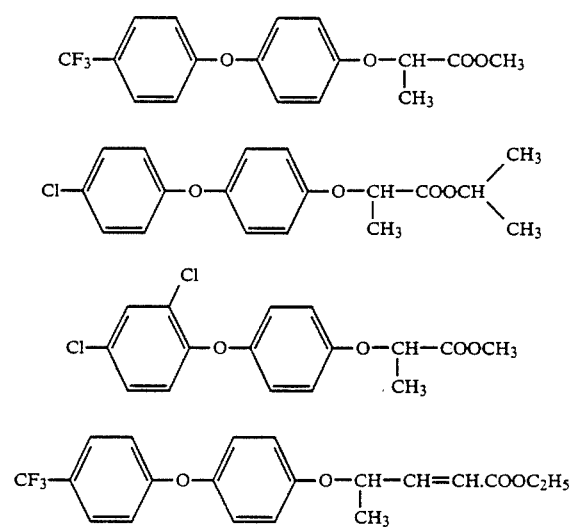

-continued

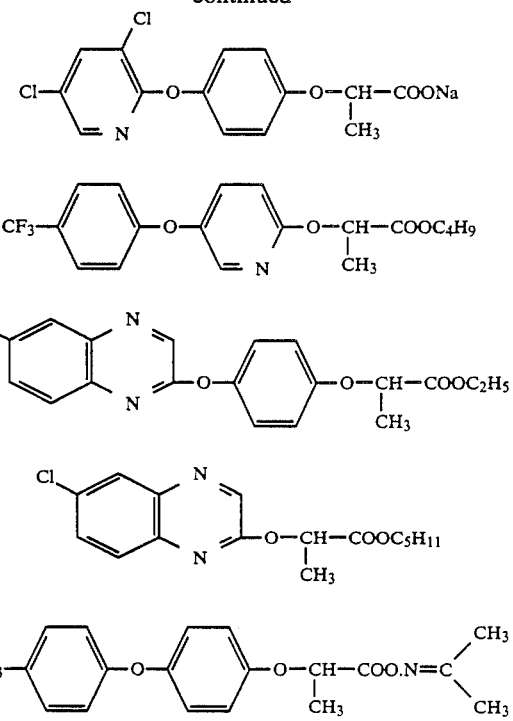

For the method of preparing crop protection agents from intermediate compounds Ia and Ib of the present invention, reference is made to the paragraph bridging pages 14 and 15 of said DOS No. 2,546,251, and the four equivalent U.S. patents of Takahashi et al. cited above with the same disclosure at column 7, about line 62, to column 9, about line 35, of each. In the present case, the monoether compound Ib corresponds to the substituted phenol (III) of Takahashi et al. and is readily obtained from compound Ia as noted above.

Further reference is made to page 1 up to page 3, line 13, of said European Patent Application No. 2,246, and the two equivalent Suchy patents, U.S. Pat. Nos. 4,200,587 and 4,380,661 cited above, each disclosing the same methods of preparing herbicidal compounds. See especially the reaction "B" at column 3, line 60, to column 4, line 23, of the Suchy patents, which describes the reaction of an oxime of the formula

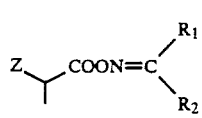

with an alcohol of the formula

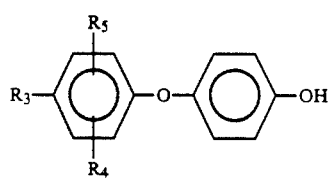

or an alkali metal salt thereof in the presence of a base. The alcohol V of Suchy corresponds to the monoether compound Ib of the present invention, which is readily obtained from the diether Ia by splitting off the tert.-butoxy group.

These methods of preparing useful crop protection agents are incorporated herein by reference as fully as if set forth in their entirety.

End products Ia which are particularly preferred as intermediates for the preparation of crop protection agents are

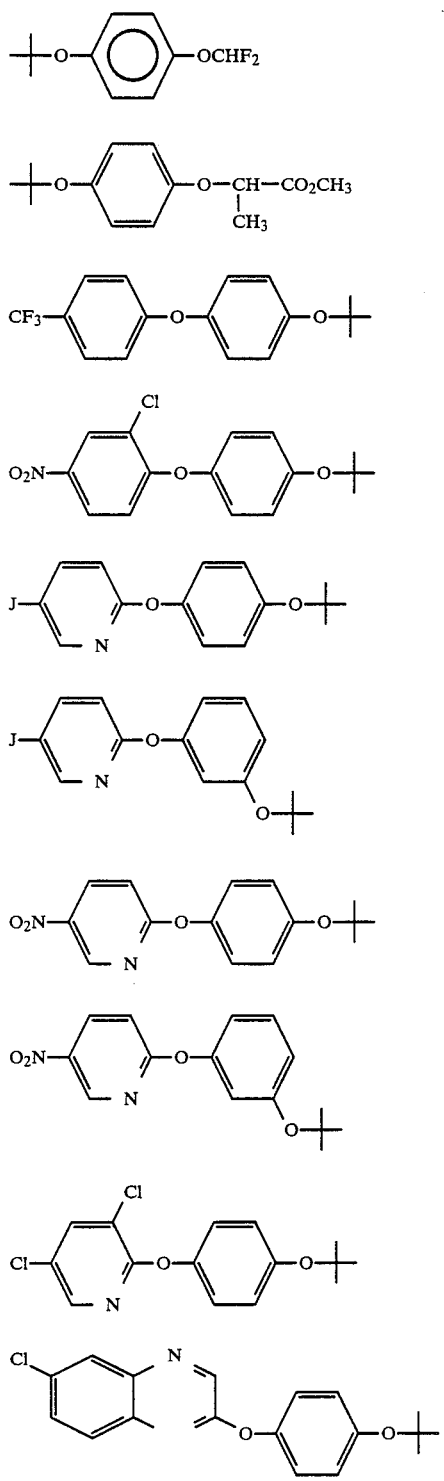

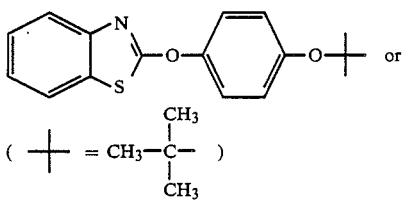

$$( \ {+}\!\!- \ = CH_3-\underset{\underset{CH_3}{|}}{\overset{\overset{CH_3}{|}}{C}}- \ )$$

In respect of the use of the compounds, reference may likewise by made to the prior art publications.

EXAMPLE 1

(a) 32 g of 2-chloro-5-nitropyridine, 33 g of p-(tert.-butoxy)-phenol, 10.5 g of calcium hydroxide and 200 ml of dimethylsulfoxide were stirred at 80° C. for 5 hours, the mixture was poured into water and brought to pH 3 with dilute sulfuric acid, and the precipitate was filtered off with suction, washed with water and dried under reduced pressure to give 53 g of 4-(5'-nitropyrid-2'-yloxy)phenyl tert.-butyl ether of melting point 109°–111° C.

(b) 13 g of the 4-(5'-nitropyrid-2'-yloxy) phenyl tert.-butyl ether obtained in Example 1a), 200 ml of ethanol, 50 g of water and 10 ml of concentrated sulfuric acid were refluxed at 78° C. for 4 hours, the mixture was cooled to room temperature, poured into water and neutralized with sodium hydroxide solution, and the precipitate was filtered off with suction, washed with water and dried under reduced pressure to give 8.5 g of 4-(5'-nitropyrid-2'-yloxy)phenol of melting point 165°–170° C.

EXAMPLE 2 a) 33.2 g of p-(tert.-butoxy)phenol, 13 g of 85 per cent strength by weight potassium hydroxide and 100 ml of methanol were refluxed at 65° C. for 1.5 hours, with stirring. The solvent was then stripped off under reduced pressure, 200 ml of dimethylsulfoxide and 50 g of 2-bromo-5-iodopyridine were added to the residue and the mixture was stirred at 120° C. for 6 hours, cooled to room temperature, poured into water and extracted with methylene chloride. The organic phase was extracted several times by shaking with water, the solvent was stripped off under reduced pressure and the residue was recrystallized from petroleum ether to give 62 g of 4-(5'-iodopyrid-2'-yloxy)phenyl tert.-butyl ether of melting point 48° C.

b) 3.0 g of the 4-(5'-iodopyrid-2'-yloxy)phenyl tert.-butyl ether obtained in Example 2a), 100 g of water, 400 ml of ethanol and 20 ml of concentrated sulfuric acid were refluxed at 78° C. for 2 hours, the mixture was cooled to room temperature, water was added and the pH was brought to 3 with dilute sodium hydroxide solution. The mixture was then extracted with methylene chloride, the organic phase was dried, most of the solvent was stripped off and the residue was crystallized by addition of petroleum ether to give 22 g of 4-(5'-iodopyrid-2'-yloxy)phenol of melting point 110° C.

EXAMPLE 3 a) The reaction was carried out in a manner similar to that in Example 1a).

b) 50 g of the 4-(5'-nitropyrid-2'-yloxy)phenyl tert.-butyl ether obtained in Example 1a), 770 ml of ethanol, 190 g of water and 10 ml of concentrated sulfuric acid were stirred at 50° C. for 4 hours. Working up in a manner similar to that in Example 1b) gave 30 g of 4-(5'-nitropyrid-2'-yloxy)phenol.

COMPARATIVE EXAMPLE 1 a) The reaction was carried out in a manner similar to that in Example 1a).

b) 50 g of the 4-(5'-nitropyrid-2'-yloxy)phenyl tert.-butyl ether obtained in Example 1a), 30 ml of 57 per cent strength hydroiodic acid and 50 ml of glacial acetic acid were stirred at 100° C. for 4 hours. Working up chiefly gave decomposition products.

COMPARATIVE EXAMPLE 2 a) The reaction was carried out in a manner similar to that in Example 1a), using the methyl ether of 4-(5'-nitropyrid-2'-yloxy)phenol instead of the tert.-butyl ether II.

b) 40 g of 4-(5'-nitropyrid-2'-yloxy)phenyl methyl ether, 770 ml of ethanol, 190 ml of water and 10 ml of concentrated sulfuric acid were stirred at 80° C. for 4 hours. Working up gave the starting substance in virtually quantitative yield.

EXAMPLE 4 a) 100 g of p-(tert.-butoxy)-phenol, 200 ml of dioxane, 240 ml of water and 112 g of sodium hydroxide were stirred at 80° C., and 80 g of difluorochloromethane were bubbled in. The reaction mixture was cooled, extracted with tert.-butyl methyl ether, dried and filtered, and the filtrate was concentrated to give 80 g of 1-(difluoromethoxy)-4-(tert.-butoxy)-benzene of boiling point 45°-50° C./0.1 mm Hg.

NMR: TMS (CDCl$_3$)
1.30 ppm (S) (9)
6.39 ppm (T) (1)
6.93 ppm (S) (4)

b) 30 g of 1-(difluoromethoxy)-4-(tert.-butoxy)benzene from Example 4a), 200 ml of ethanol, 50 ml of water and 10 ml of concentrated sulfuric acid were stirred at 80° C. for 2 hours. The reaction mixture was extracted with ether, the organic phase was dried and filtered, and the filtrate was concentrated to give 16 g of 4-difluoromethoxyphenol.

NMR: TMS (CDCl$_3$)
4.12 ppm (S) (1)
6.35 ppm (T) (1)
6.72 ppm (D) (2)

6.95 ppm (D) (2)

We claim:

1. A diether of the formula

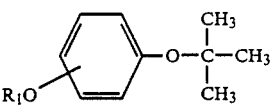

where the two ether groups are in the m- or p-position relative to one another and R$^1$ has one of the formulas:

$$\begin{array}{c} R^2\ O \\ |\ \ || \\ -C-C-OR^2 \\ |\\ R^2 \end{array} \quad \text{or}$$

(benzene ring with four R$^3$ substituents)

wherein the individual groups R$^2$ and R$^3$ can be identical or different and each is hydrogen, alkyl of 1 to 6 carbon atoms which is unsubstituted or substituted by 1 or 2 chlorine and/or fluorine atoms, aralkyl or alkylaryl of 7 to 12 carbon atoms or aryl of 6 to 10 carbon atoms, and R$^3$ can also in each case be halogen, nitro, trifluoromethyl, trichloromethyl, cyano or alkoxy provided that each of nitro, trifluoromethyl, trichloromethyl and iodine are not polysubstituted.

2. A diether of the formula (structure: R$^1$O—C$_6$H$_4$—O—C(CH$_3$)$_3$)

where R$^1$ is —CH(CH$_3$)COO—R$^2$ and R$^2$ is alkyl of 1 to 6 carbon atoms.

3. The diether of the formula (structure: 2,4-dichlorophenyl 4-(tert-butoxy)phenyl ether)

* * * * *